(12) United States Patent
Strizzi et al.

(10) Patent No.: US 8,386,404 B2
(45) Date of Patent: Feb. 26, 2013

(54) METHODS FOR AUTOMATED EDDY CURRENT NON-DESTRUCTIVE TESTING ANALYSIS

(75) Inventors: Jeff Strizzi, Kirkland, WA (US); Tom Matelich, Spokane, WA (US)

(73) Assignee: Zetec, Inc., Snoqualmie, WA (US)

( * ) Notice: Subject to any disclaimer, the term of this patent is extended or adjusted under 35 U.S.C. 154(b) by 568 days.

(21) Appl. No.: 12/689,576

(22) Filed: Jan. 19, 2010

(65) Prior Publication Data
US 2010/0185576 A1 Jul. 22, 2010

Related U.S. Application Data

(60) Provisional application No. 61/145,666, filed on Jan. 19, 2009.

(51) Int. Cl.
G06F 15/18 (2006.01)
G01B 5/28 (2006.01)
F16L 55/00 (2006.01)
F16L 35/00 (2006.01)

(52) U.S. Cl. .............. 706/20; 702/35; 138/36; 285/93
(58) Field of Classification Search ................ None
See application file for complete search history.

(56) References Cited

U.S. PATENT DOCUMENTS

| | | | |
|---|---|---|---|
| 5,430,376 A | 7/1995 | Viertl | |
| 2004/0113625 A1* | 6/2004 | Pagano et al. | 324/334 |
| 2007/0219757 A1 | 9/2007 | Papadimitriou et al. | |
| 2010/0008462 A1 | 1/2010 | Killian et al. | |
| 2010/0102808 A1 | 4/2010 | Boenisch | |
| 2010/0307249 A1* | 12/2010 | Lesage et al. | 73/623 |

FOREIGN PATENT DOCUMENTS

WO 2004066044 A1 8/2004

OTHER PUBLICATIONS

Zetec, Inc., "RevospECT Product Overview", Dec. 31, 2008, XP002588076, Retrieved from the Internet: URL: http://www.zetec.co.kr/ (23 pages).
International Search Report for PCT/US2010/021428 mailed Jul. 8, 2010.

* cited by examiner

Primary Examiner — Alan Chen
(74) Attorney, Agent, or Firm — Caesar, Rivise, Bernstein, Cohen & Pokotilow, Ltd.

(57) ABSTRACT

A system and method for precisely detecting tubing flaws using a computer architecture that combines scalable processing power with an extensible array of detection and classification possibilities involving eddy current data analysis, as well as detection algorithms for pinpointing exact tubing regions and wherein these regions can be further divided into manageable segments for flaw analysis. Multiple classification tools utilized to discriminate detection and to precisely assign proper report codes to detect flaws repeatedly and accurately.

10 Claims, 17 Drawing Sheets

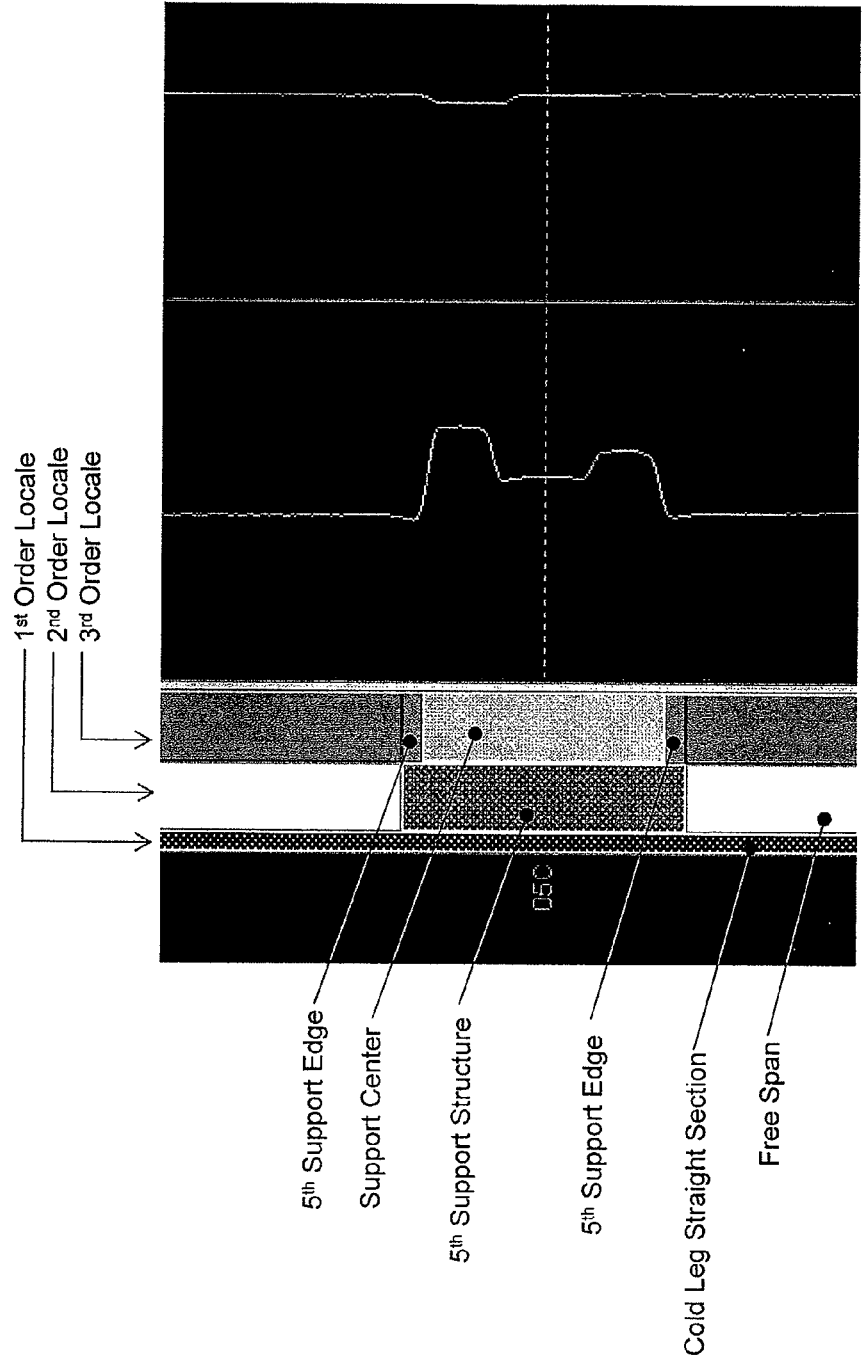

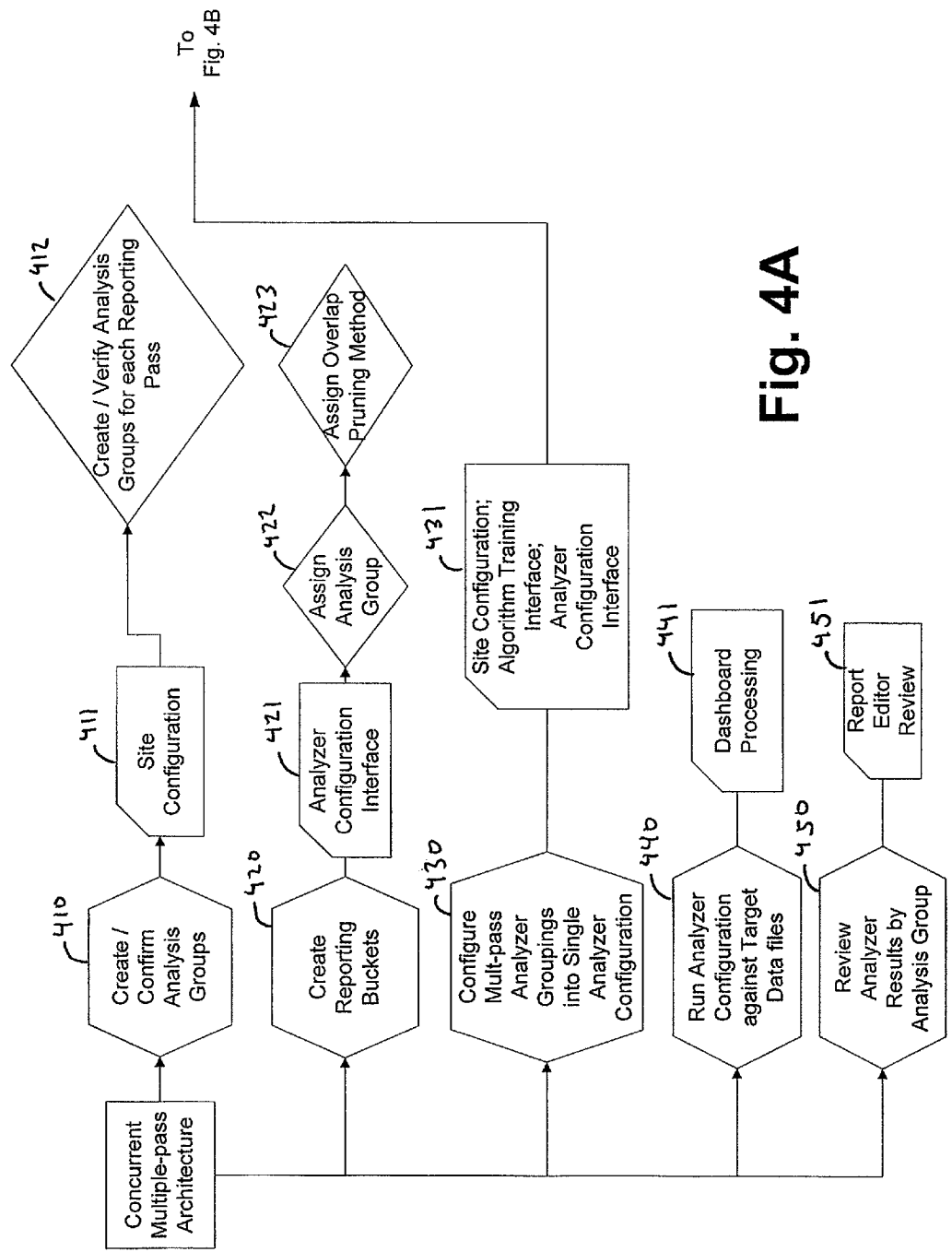

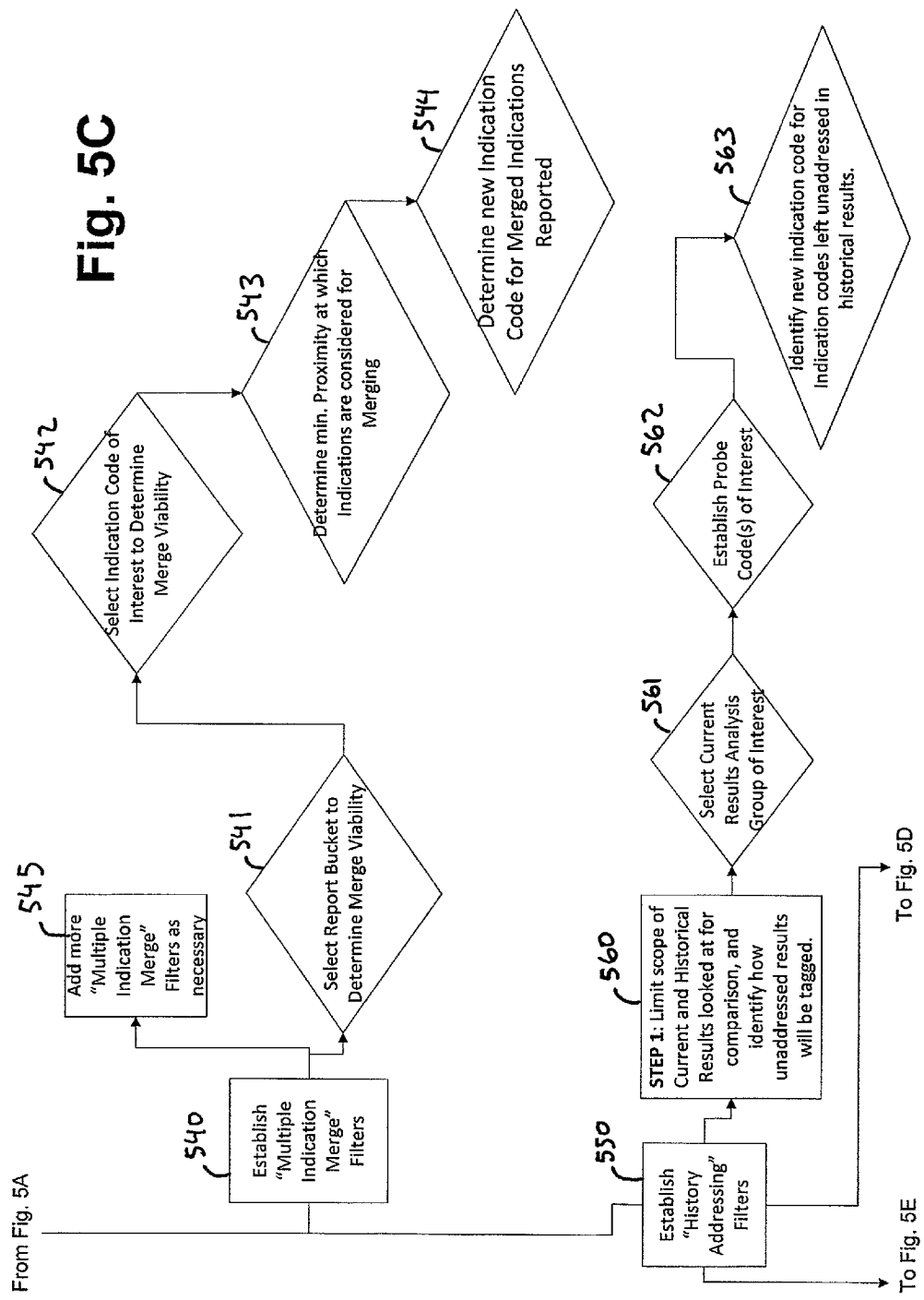

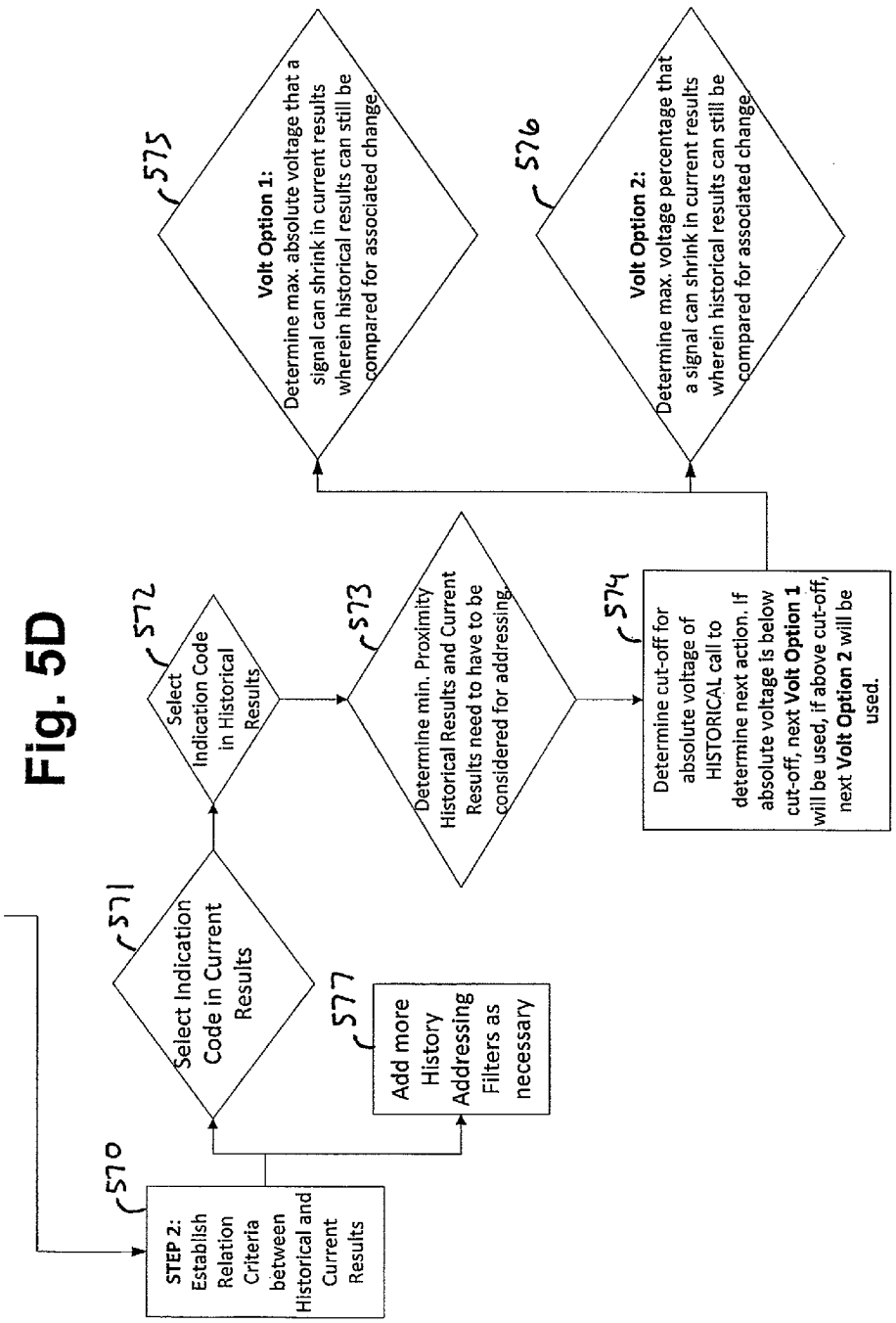

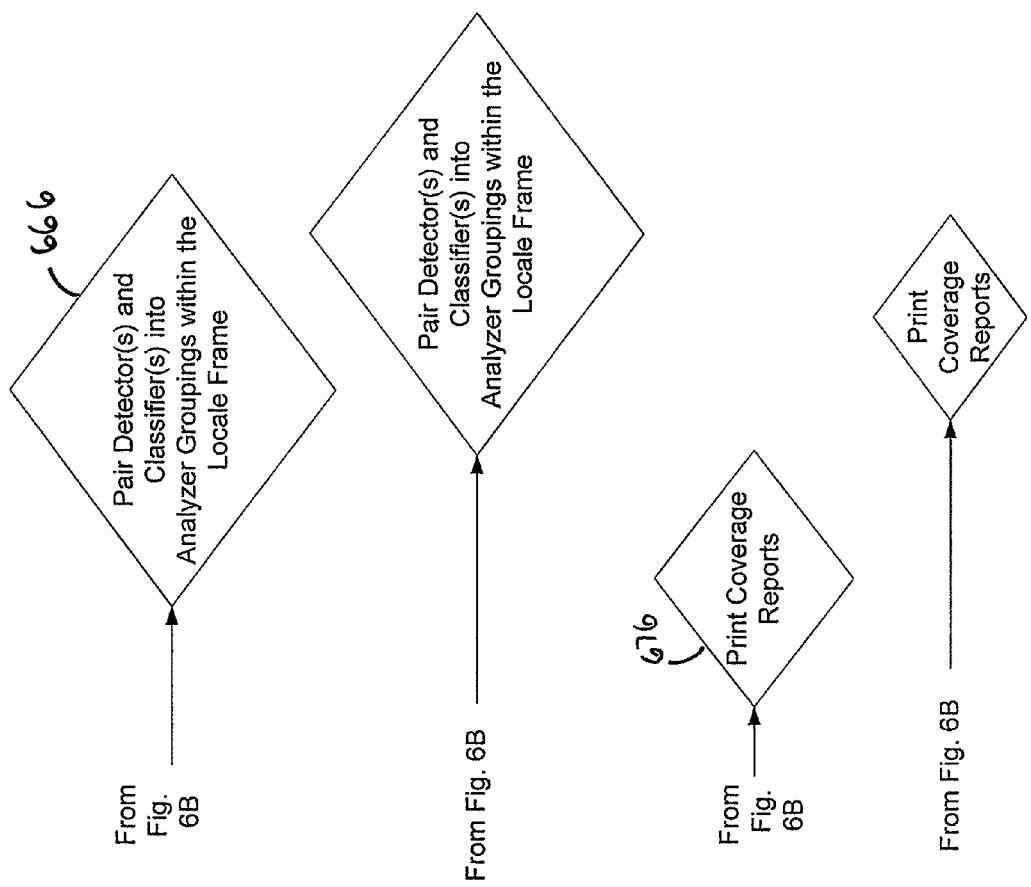

METHODS FOR AUTOMATED EDDY CURRENT NON-DESTRUCTIVE TESTING ANALYSIS

CROSS-REFERENCE TO RELATED APPLICATIONS

This application claims priority to, and the benefit of U.S. Provisional Application No. 61/145,666 filed Jan. 19, 2009 for all matter common to both applications. The disclosure of said provisional application is hereby incorporated by reference in its entirety.

BACKGROUND OF THE INVENTION

1. Field of Invention

The present invention relates to automatic monitoring and analysis systems and more particularly to a system and method for precisely detecting tubing flaws using a computer architecture that combines scalable processing power with an extensible array of detection and classification possibilities involving eddy current data analysis, as well as detection algorithms for pinpointing exact tubing regions and wherein these regions can be further divided into manageable segments for flaw analysis.

2. Description of Related Art

In the field of automated monitoring and analysis systems and processes, there remains a need for an architecture that combines scalable processing power with an extensible array of detection and classification possibilities and especially where eddy current data analysis is required and where the need for quality of work performed must be verified. Where process tube flaws are involved, there remains a need for pinpointing exact regions of the tubing whereby such regions can be further divided into manageable segments which provide clear and precise regions for flaw analysis. There also remains a need for the use of classification tools which can be configured to discriminate detection and precisely proper report codes for detecting flaws repeatedly and accurately.

All references cited herein are incorporated herein by reference in their entireties.

BRIEF SUMMARY OF THE INVENTION

A system for the comprehensive monitoring, analysis and managing of tubing flaws wherein the system comprises: a computer platform whose architecture involves a distributed processing system for supporting parallel execution of automated analysis tasks, and wherein the platform comprises a locale analyzer and a detection classification unit for pinpointing tubing flaws; means for channel aliasing for analyzing data in terms of a particular class of datastream; an auto final acceptance means that automatically applies analyst-configured rules to reduce forms of overcall that would result from using high probability of detection automated analysis methods; and locale mapping means for generating settings to certain areas of the tubing and associated components, wherein the locale mapping means implements landmark edge correction, mapping a damage mechanism to a plurality of related analysis locales, and algorithms that involve expansion transition detection, adaptive threshold detection and locating schemes.

A method for the comprehensive monitoring, analysis and managing of tubing flaws. The method comprises: loading and calibrating historical data and acquired data on a computer platform; sorting the historical and acquired data by locale; mapping the data for generating settings to certain areas of the tubing and associated components; detecting flaws based on the mapped data; classifying the flaws using any number of ratio or direct difference measurements between frequencies for voltage, angle, depth and length; and applying analyst-configured rules for reducing various forms of overcall and for selecting a single final result to report from among many redundant results.

BRIEF DESCRIPTION OF SEVERAL VIEWS OF THE DRAWINGS

The invention will be described in conjunction with the following drawings in which like reference numerals designate like elements and wherein:

FIG. 1d shows locale segmentation mapped for a support structure

FIGS. 4a-b are a block diagram of a concurrent multi-pass architecture;

FIGS. 5a-5e are a block diagram of a final acceptance process flow; is a block diagram of a concurrent multi-pass architecture; and FIGS. 6a-6c are a block diagram of multi-algorithm analysis management.

DETAILED DESCRIPTION OF THE INVENTION

Figure 1:
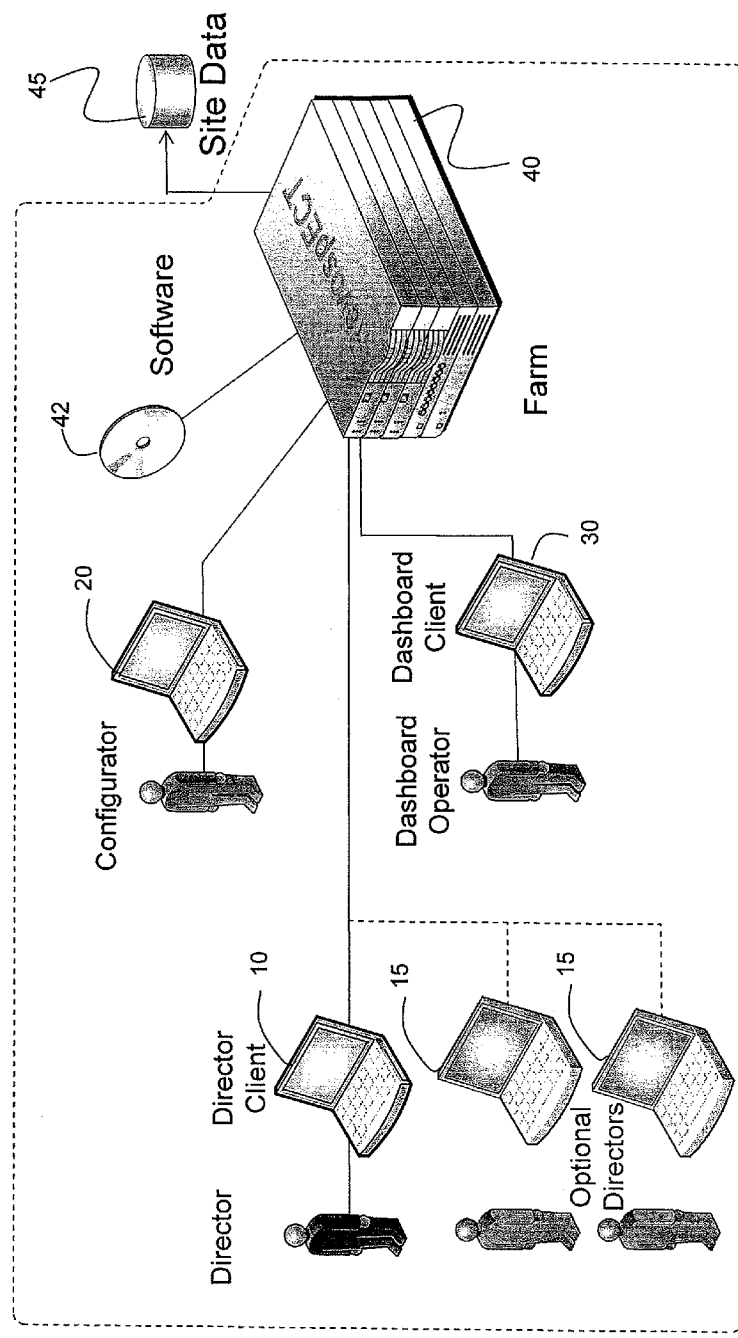
FIG. 1 is a functional diagram of a system implementing the methods of the present invention.

FIG. 1 is a block diagram of an exemplary system implementing the method of the present invention. This method and/or system of the present invention may also be referred to the Assignee's (namely, Zetec, Inc.) internal acronym "RevospECT".

Figure 2:
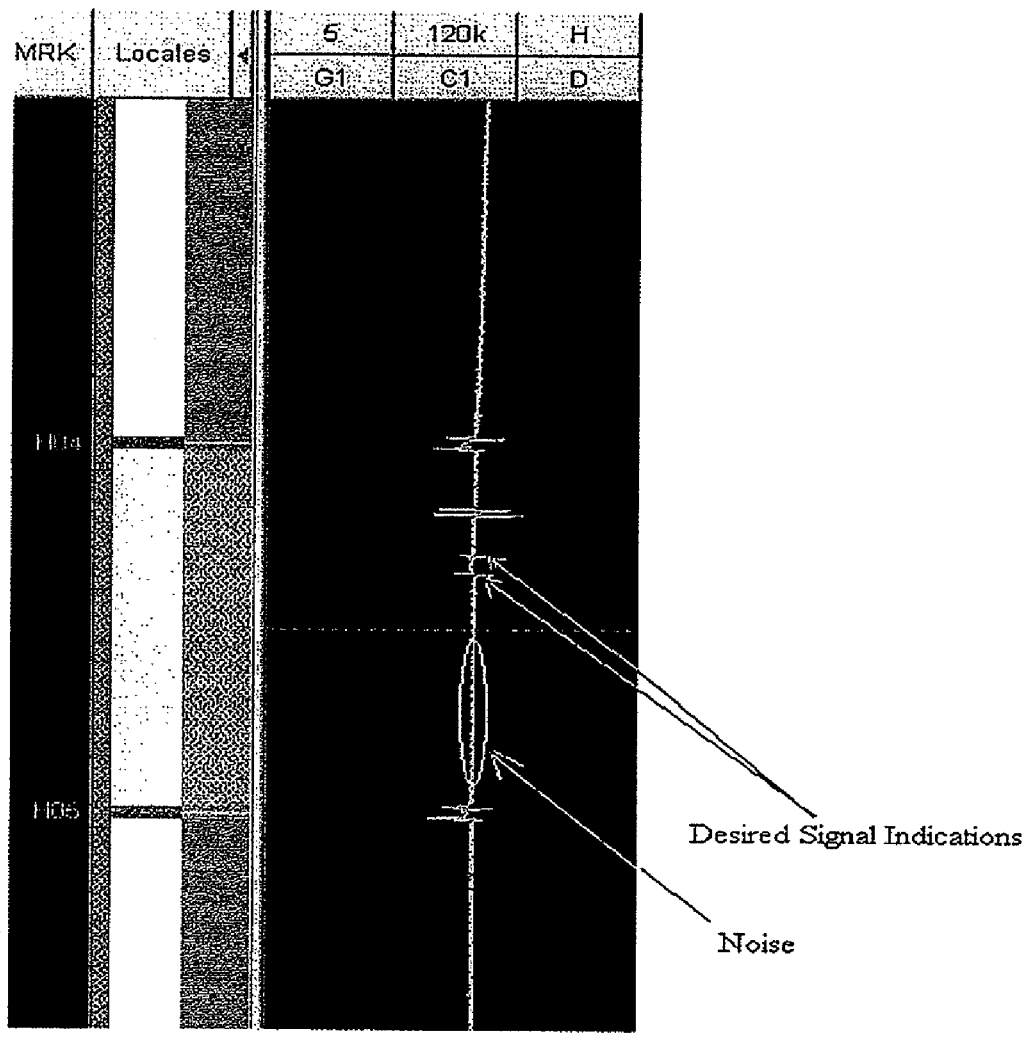
FIG. 2 depicts a sub-section of a differential bobbin signal showing a noise region and desired signal indications.

FIG. 2 is a flow diagram of a method for analyzing eddy current test data. The system/method 20 of the present invention involves the use of architecture, channel aliasing, final acceptance, locale mapping and a training user interface. Each of these components is discussed below.

System Architecture

Processing Farm

With respect to FIG. 1, the system hardware includes a distributed processing system (farm) 40 to handle parallel execution of many automated analysis tasks and is used to meet throughput goals. The design goals were low network overhead and expandability. The farm comprises Windows operating system-based file servers on which are used to access raw data 45 and setups. In the present invention, the input to the farm is the UNC path to the data 45 and the necessary setup files, plus a SQL server connection string and parameters to find data in the database.

A "Processing Farm" consists of 4 components:

1. The client is the software the analyst uses to submit jobs to the farm for completion. It is run on the analyst's machine. FIG. 1 shows three types of clients, the director client 10, the dashboard client, 30 and the configurator 20.

2. The scheduler receives the jobs to be performed and distributes them among its processing nodes. The scheduler is fairly low overhead network- and CPU-wise, and may be run on any computer accessible by all nodes and clients.
3. A processing node runs on each computer and executes 1-N processing applications. N defaults to the number of CPU cores detected on the machine.
4. A processing application performs work, reporting progress, sending status messages, and final completion success/failure.

Due to the simple design developed for the client to request work, the farm is actually generic to any processing application. There is a dll which has an interface class to be implemented by a processing application to meet communication requirements. An instance of the processing node is tied to one particular type of processing application, but multiple nodes could be run on one computer.

The farm provides a way to meet the goals for data throughput by permitting the performance of many analyses at the same time.

Top Level Project Flow

Figure 1A:
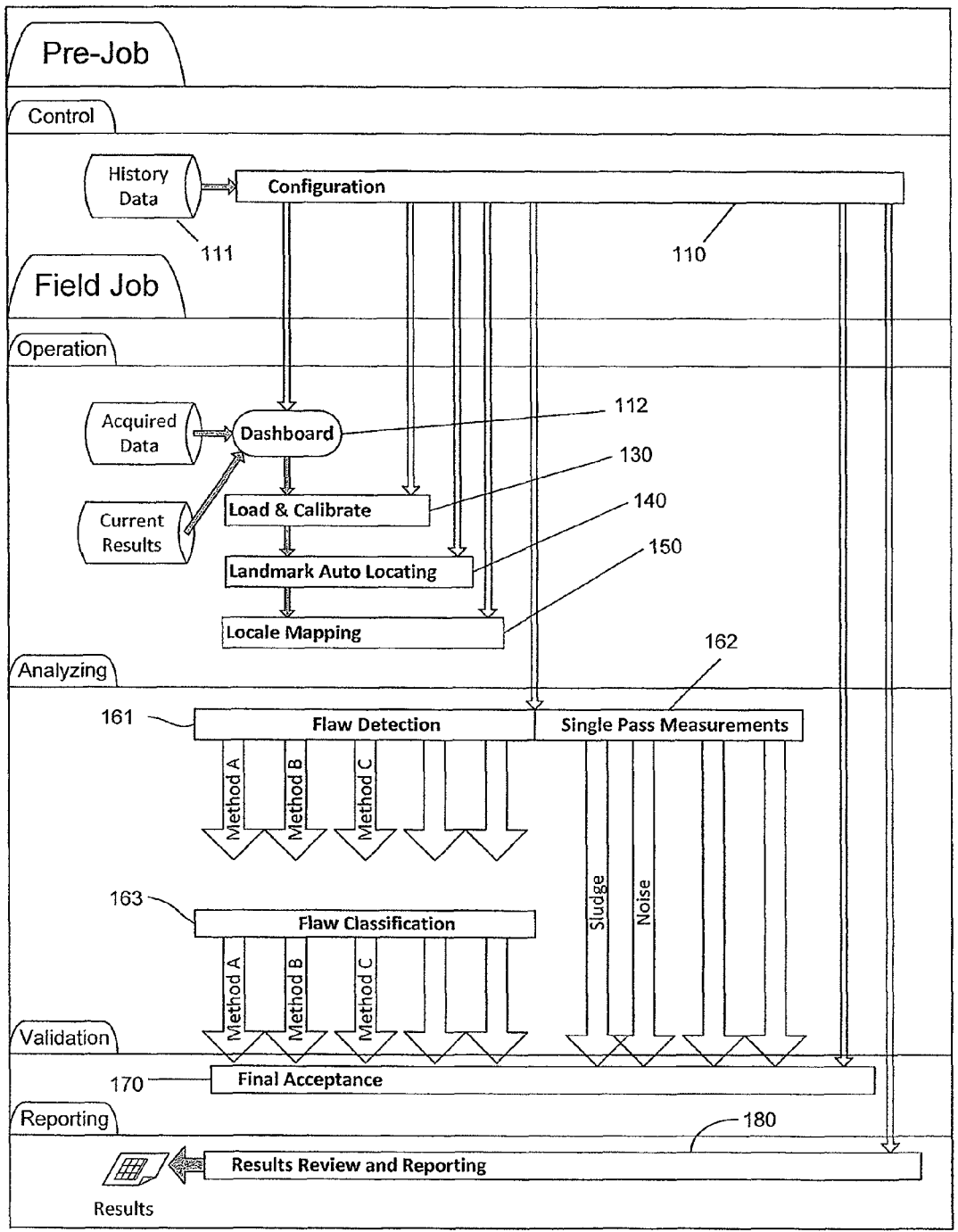
FIG. 1a shows a top-level flow diagram for a system implementing the methods of this invention.

FIG. 1a is a process diagram showing the main processes of a system implementing the inventive methods described herein.

Figure 1B:
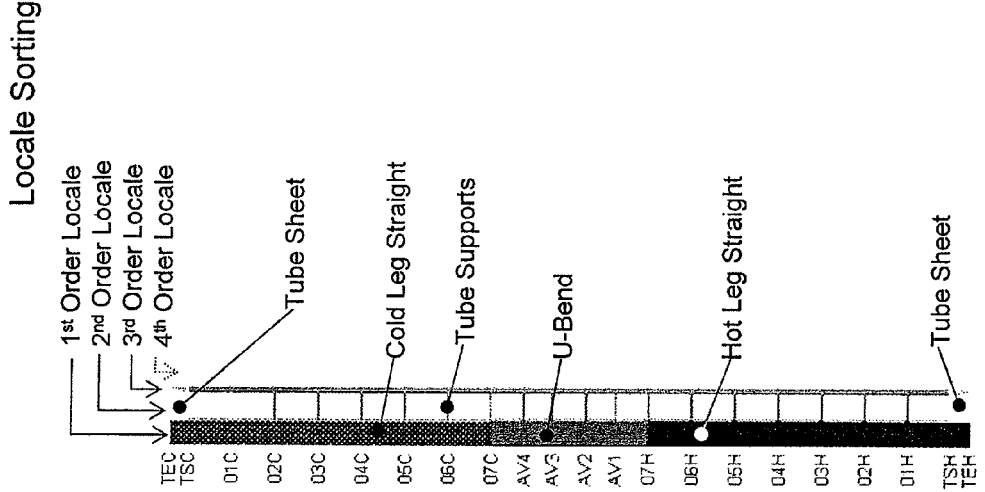
FIG. 1b shows exemplary locale mapping at multiple levels
Figure 1C:
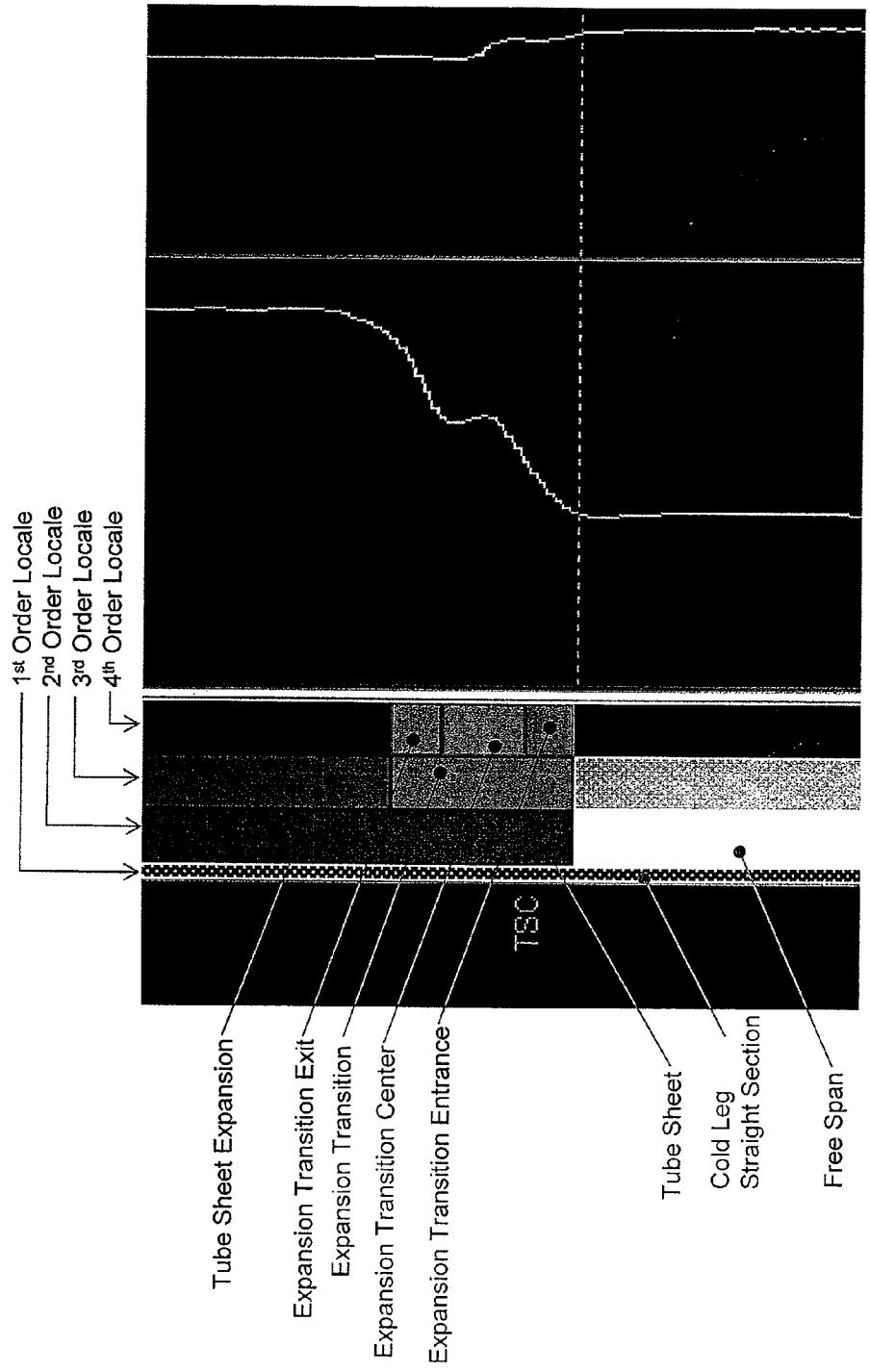
FIG. 1c shows locale segmentation mapped for a tube sheet expansion

In the Pre-job Configuration 110, channel aliases are configured, locales are set up, detectors are defined, classifiers are defined and detectors and classifiers are mapped to locales. The meanings of these terms are explained in detail below. Previous history data 111 is also imported in the Pre job Configuration. Previous history data enables report comparisons, supports validation of damage reports and supports morphology tracking. Channel aliasing provided descriptive channel naming that is independent of specific variables, and it provides portability of channels into detectors and classifiers. Locales can be defined in multiple levels as shown in FIGS. 1b-1d.

Detectors are also configured in the Pre job configuration. Multiple detectors can be defined for a system to meet specific qualified technique parameters. The system's extensible architecture allows multiple detection modes based on a variety of algorithms, including rule-based and adaptive threshold detection algorithms. Classifiers are also configured in the Pre job configuration. Classifiers can be set up using multiple classification rules for multiple test conditions and equal/not-equal rules. Classification algorithms include rule-based methods and a polar coordinate discriminator. The mapping of detectors and classifiers to locales is achieved by setting up relationship rules. Multiple detectors can be assigned to a single classifier. Detector and classifier sets can be assigned to multiple locales at various levels of detail. Multiple detectors and classifiers combinations can be made with Boolean terms. FIG. 1d shows how detectors and classifiers are applied to various locales.

After the pre job configuration is complete, the configuration is locked and job production can begin. The process elements of this phase are shown in FIG. 1a under the headings Operation, Analyzing, Validation and Reporting.

During the Operation, a Dashboard client 112 is used to select a data server, map network drives, load calibration groups, monitor the job progress queue and display alerts on calibration groups in process. Examples of alerts are, pause, working and failure. Individual file alerts include: submitted, begin analysis, awaiting, complete and failed.

The load and calibrate phase 130 of the Operation involves automatic calibration to a calibration standard. Similar standards can be loaded together. Flaws from multiple standards can be joined together and used in a calibration group.

Landmark automatic locating 140 and locale mapping 150 are also performed as part of the Operation phase.

In the analysis phase, flaw detection 161, flaw classification 162 and single pass measurements 163 for effects like sludge and noise are made. Data flows through detection 161 and classification 163 before processing through single pass measurements. Data is divided into locales based on configuration. Detection is applied to Locales based on configuration. Classification is applied to detected flaws based on configuration and classified flaws are written to "buckets" for final acceptance.

In the noise measurement analysis, detected flaws are suppressed. Noise values are measured by locale and technique. Noise is measured based on raw data. Modes of noise measurement include peak-to-peak voltage, vertical maximum and horizontal maximum. A maximum noise value per locale can be assigned. In one embodiment, only noise that exceeds a pre-set threshold is recorded.

Final acceptance 170 is run after the analysis phase. In final acceptance, overlaps are resolved by determining which conditions to report based on historical conditions in combination with other criteria if desired. A proximity filter allows multiple conditions within a predetermined space to be combined and indicated as a single condition. A historical report comparison is also made during final acceptance and changes from previous reports are flagged and reported. Noise measurements are also reported for the localizes area of a reported flaw to support signal-to-noise reporting.

The final stage of the field job process is the reporting phase 180. At this stage, site-specific reporting filters can be applied.

Multiple Algorithm Architecture

The basis of the auto analysis core architecture is in pre-determining the critical locations of analysis within the tube and providing the flexibility to combine any number of detection algorithms with any number of classification algorithms in each of these specific regions to allow for maximum probability of detection of our damage mechanisms. The architecture also achieves complete control over guaranteeing that every slice of the tube has been analyzed and exactly where and how any analysis overlap occurs. The architecture provides the flexibility to analyze at any level of location granularity, so for instance, one can look very specifically for a damage mechanism in the tubesheet expansion transition, or perform a more general scan of the entire tubesheet region, or both.

Figure 6A:
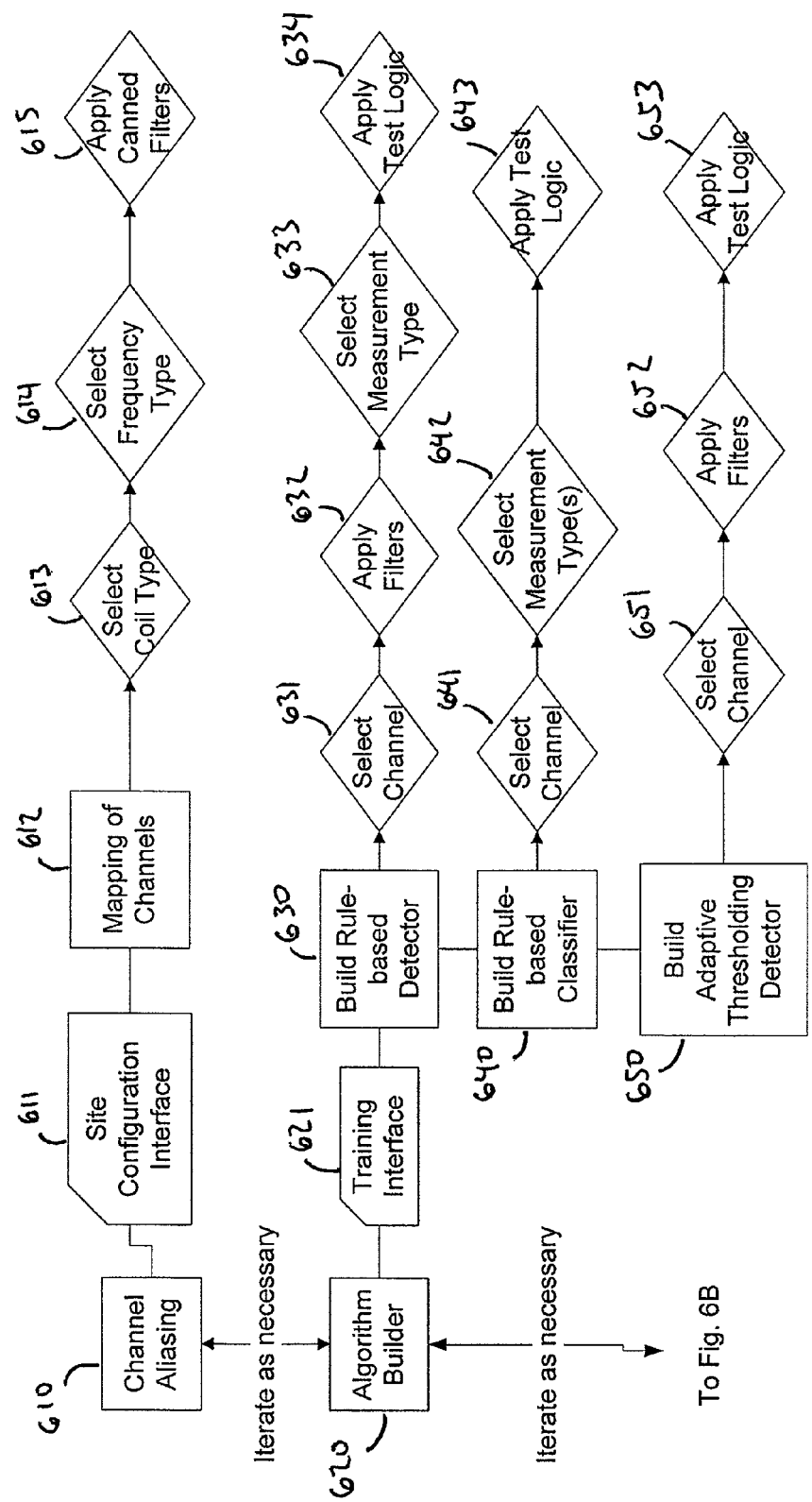
Figure 6B:
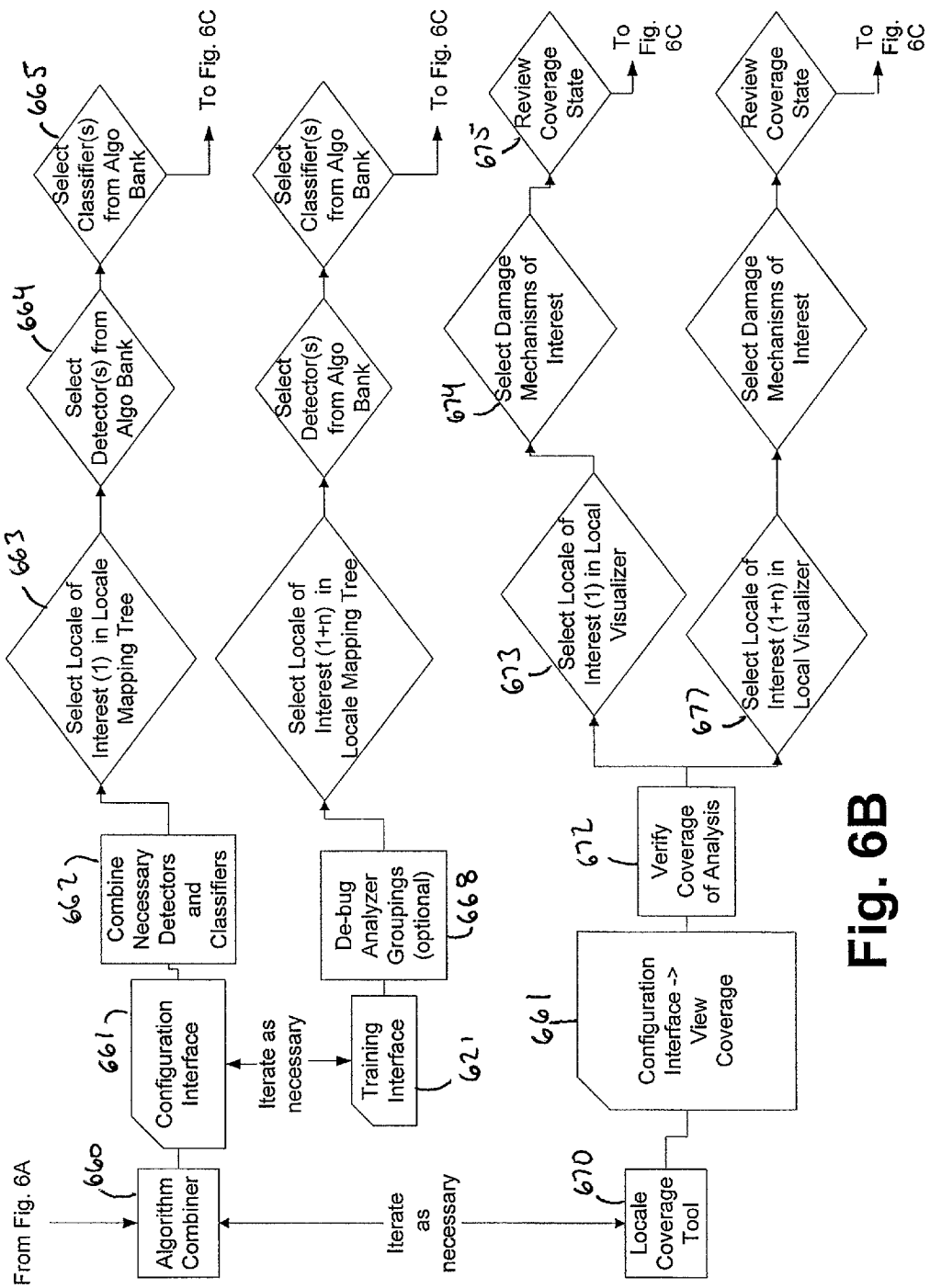

The Multiple Algorithm Analysis Management is described in the flow diagrams FIGS. 6a-6c. Channel Aliasing: ☐Objective of Channel Aliasing is to enable creation of channel setups that are reusable. Reusability has two critical benefits: 1) Higher confidence that best practices will be employed and reemployed and 2) Reduced job preparation time due to leveraging preexisting configuration elements.

Algorithm Builder: All RevospECT algorithms are configured in the Revospect training interface, which provides a means to create detection and/or classification algorithms and test them on live data. During testing of the algorithm, key algorithmic steps such as dynamic threshold determinations, measurement locations, angle and voltage determinations, pass/fail status, etc. are stored in the program for subsequent review by the operator. Thus, the operator may step forward and back through the analysis process at will and view the exact details of how the currently configured algorithm performed its analysis. At each step information may be available to the system to automatically train in or out a signal of interest.

Algorithm Combiner: All RevospECT algorithms are organized and applied for analysis to the specifics of a target steam generator in the Algorithm Configuration Interface.

The steam generator is defined into regions of interest, called Locales. Specific combinations of Detector and Classifier algorithms (built in the Algorithm Builder) are combined and applied to Locales of interest (based on customer guidelines for analysis). Combinations of Detector and Classifier Algorithms that are applied to specific Locales are called Analyzer Groupings. Analyzer Groups are created to look for specific Damage Mechanisms of interest that are defined in the customer guidelines for analysis.

Locale Coverage Tool: The Algorithm Configuration Interface renders visual representations of all Locales, and color-codes Locales based on state of Analyzer Grouping coverage for each Locale. The Locale Coverage Tool represents all Locales by each Damage Mechanism of interest based on customer guidelines for analysis. In addition to a visual representation, the Locale Coverage Tool ties into each view a text-based summary of the Analyzer grouping associated for each Locale, by each Damage Mechanism Multi-algorithm analysis proceeds as follows:

Channel Aliasing 610 is performed at a site configuration interface 611. through which channels are mapped 612. In the channel mapping stage, for each channel, a coil is selected 613 a frequency type is selected 614 and predetermined filters are applied 615.

There is a significant amount of variation in eddy current inspection parameters across generators and customers, from tubing variations and site preferences. However, analysis of the data has a large degree of commonality due to the basics of eddy current analysis. To permit working in generalities while targeting site specific situations when configuring analysis of data, the channel alias was created. It essentially permits analyzing data in terms of the concept of a particular class of data stream. For example, bobbin detection of flaws will generally take the prime frequency differential channel into consideration. This may be channel 1, 3, or even 169 for the bobbin coils of an XProbe. It will have varying frequencies depending on the generator. However, each of these instances can be referred to as BobbinDiff.High. Each acquisition technique has a mapping of actual channel to alias.

For process channels, there is a list of names indicative of the purpose of the process channel. The alias also supports adding on named data filters. A collection of filter settings are named by the user, and may be specialized per technique. This specialization provides the ability to adjust filters based on specifics like pull speed. For example, a median filter needs its window adjusted based on sample density. In addition, 301 slices can be defaulted to, but increase or decrease as necessary for different settings.

The aliases then are used for detection and classification settings. This allows the settings to target the damage mechanisms basic presentation and be taken from one technique to another with minimal modification.

The Algorithm Builder 620 stage is implemented through a Training Interface 621. A rule based detector 630 is built in this phase, which, as described above, includes selecting a channel 631, applying filters 632, selecting a measurement type 633 and applying test logic 634. Multiple detector configurations can be defined in the system. Detectors can be configured to meet specific qualified technique parameters Current Algorithms: Michigan State adaptive threshold Rule based algorithm with continuous wavelet transform filter; or a Zetec Custom Rule Based algorithm.

A rule based classifier 640 is also built in the algorithm builder phase 620 through the training interface 621. The building of a classifier involves selecting a channel 641, selecting a measurement type 642 and applying test logic 643.

An adaptive thresholding detector 650 is also built in the algorithm builder phase 620 through the training interface 621. The building of a thresholding detector involves selecting a channel 641, applying filters 652 and applying test logic 653.

The algorithm combiner 660 is implemented through a configuration interface 661 to combine necessary detectors and classifiers 662. A locale of interest is selected in a locale mapping tree 663. Next, detectors 664 and classifiers 665 are selected 664 from an algorithm bank. Detectors and classifiers are then paired into analyzer groupings within the locale frame 666. Through the training interface 621, analyzer groupings cane be debugged 668 and the combination process repeated if necessary as shown.

Locale coverage is performed by a locale coverage tool 670 which operates through the configuration interface 661. Coverage of Analysis 672 is verified by selecting a first Locale of Interest 673 in a Visual Localizer, selecting damage mechanisms of interest 674, reviewing coverage state 675 and printing coverage reports 676. This process can be repeated for additional locales 677.

The Configurator client 20 defines detectors, discriminators and classifiers per locale. Specific locales are configured collectively or independently Individual locales are defined for detection, discrimination & classification Multiple detectors, discriminators and classifiers are set with and/or logic. Classification Codes are assigned based on configuration Locales Accurately defined locales are essential for an effective analysis process. This involves sub-division of tubes into locales requires accurate landmark detection. =Automatic landmark detection using multiple advanced algorithms provides precision in landmark detection A multi-stage automatic landmark structure detection (FIG. 1d 140) process is used: Stage 1 Parse data with configuration Landmark Table. Stage 2 Parse data using landmark detection algorithms to produce accurate structure locations Stage 3 Subdivide structures into specific locales. Locales are defined in multiple levels: 1st Order Locales are typically tube regions e.g.: HL, CL and U-Bend. 2nd Order Locales are typically proper structure regions e.g.: support plate, tube sheet and free span. 3rd Order Locale are typically structure sub-divisions e.g.: tube sheet expansion, tube sheet expansion transition, support center and support edge. 4th Order Locales are typically transition divisions e.g.: expansion transition center, expansion transition entrance and expansion transition exit. See FIGS. 1b-1d regarding locale sorting.

Analysis Locale

The AnalysisLocale is the data structure which describes a single or aggregate area within the tube. It can describe any level of granularity, as the following examples suggest:

1. FullTube/HotLeg (the entire hot leg)
2. FullTube/Ubend//FreeSpan (each separate piece of free span contained in the ubend)
3. FullTube/HotLeg/Tubesheet/Expansion (just from beginning to end of the hot leg expansion transition)
4. FullTube/ColdLeg/FreeSpan/SludgePile (from the beginning of the free span to the top of the sludge pile)
5. FullTube/Ubend/UbendStructures/StructureEdges (just the edges of the structures in the ubend)

6. FullTube/Ubend/UbendStructures (the full structure signals in the ubend, including the edges and centers)

All locales and necessary levels of granularity are anticipated and packaged in an xml file. Each of these anticipated locales employ the algorithms necessary to map it to set of slice values within the tube, such that no slice gaps between mapped locales will be possible. The code ensures that each successive level of granularity is fully contained within the parent and that every slice of the parent locale is accounted for by an immediate child locale.

The Locale Analyzer

The LocaleAnalyzer is responsible for initiating analysis on a single AnalysisLocale. It contains and applies to exactly one AnalysisLocale, and contains an array of specific analysis methods (LocaleAnalyzerUnits) to perform on the entirety of that locale. The AnalysisLocale also contains an array of smaller granularity AnalysisLocales, each pertaining to an area bounded within its own locale as described by the AnalysisLocaleTree. The LocaleAnalyzerUnit is the abstract base class responsible for any type of single analysis pass on a given AnalysisLocale. Each LocaleAnalyzerUnit has a single designated AnalysisReportBucket which may or may not be shared with other LocaleAnalyzerUnits depending on the user configuration.

The following classes derive from LocaleAnalyzerUnit:
1. SludgeReportUnit
2. NoiseMeasurementUnit
3. DetectionClassificationUnit The AnalysisReportBucket is a collection of related results. All results placed in the same AnalysisReportBucket are automatically checked for spatial overlap against other results in that bucket. If the locations for two results are found to overlap, then one of the results is pruned out as determined by a user configured rule of either:
1. First in—the first report entry in the bucket will remain and the newer one will be discarded.
2. Last in—the last report entry to be added will remain and the older one will be discarded.
3. Biggest volts—whichever entry has the largest volts measurement (as reported in the intermediate report entry structure) will be kept and the smaller one discarded.
4. Biggest footprint—whichever entry has the larger spatial footprint will be kept and the smaller one discarded.

During auto analysis configuration, the user will create any number of AnalysisReportBuckets, one of which will be chosen for each LocaleAnalyzerUnit. Typical AnalysisReportBuckets are as follows:
1. Dents
2. MBMs (manufacturing buff marks)
3. Flaws
4. Sludge (reserved for internal use only)
5. Noise (reserved for internal use only)

The intent is that the user wants to have dents, mbms, sludge, etc. called regardless if they overlap with other types of report entries. The AnalysisReportBuckets is also used later during the final acceptance stage to determine what to do with overlapping entries which are not within the same bucket, but which may still want to be pruned based on additional rules or which may need to have the indication code changed based on it overlapping with something from another bucket (like a dent, for instance).

Detection Classification Unit

The DetectionClassificationUnit is a form of LocaleAnalyzerUnit which contains a single DetectionStep and a single ClassificationStep. The DetectionClassificationUnit is informed by the LocaleAnalyzer to initiate analysis via the DetectionStep, and then waits for the DetectionStep to finish (each detection algorithm is on a separate thread), then initiate classification via the ClassificationStep, then similarly wait for the ClassificationStep to finish.

Detection Step

The DetectionStep class represents a composite detection scan of an analysis region. It can be made up of multiple independent detection passes and will result in a single array of DetectionResults. Each pair of neighboring results will be handed over to a DetectionMerger object which has been configured to merge the results either by combining if they overlap or throw out anything that doesn't overlap. An (overcomplicated and unlikely) example of the detections with corresponding detection merge rules is as follows:
DET1 'and' DET2 'or' DET3 'or' DET4 'and' DET5 'and' DET6.

Detection Result

The DetectionResult is a simple data structure designed to describe a rectangular or one dimensional location in the data. It will have a lifespan limited to the time between detection and classification.

Detector

The Detector is the base detection class, from which will be derived the other various styles of detector, including PlugInDetector, ZRBDetector, and MatlabDetector. The output of the Detector is a vector of DetectionResults.

Detection Merger

The DetectionMerger is the functional class responsible for implementing either 'or' logic or 'and' logic on two DetectionResults. The result of any single operation is another DetectionResult, which may then need to be combined with another DetectionResult. The method for combining any complexity of DetectionResults with their corresponding DetectionMerger rule is to operate on all 'AND' terms first, and always from left to right. So given the earlier example of:
DET1 'and' DET2 'or' DET3 'or' DET4 'and' DET5 'and' DET6

The operations are:
1. Perform DET1 'and' DET2 (result=DET12)
2. Perform DET4 'and' DET5 (result=DET45)
3. Perform DET45 'and' DET6 (result=DET456)
4. Perform DET12 'or' DET3 (result=DET123)
5. Perform DET123 'or' DET456 (result=DET123456)

The definition of 'and' is as follows: For any two DetectionResults, only that portion of them which overlaps with the other is kept and becomes a new single DetectionResult. The definition of 'or' is as follows: for any two DetectionResults, all results are kept unmodified except where they overlap (meaning that at least N % of each result is contained within the other result, where N is configurable). When two DetectionResults overlap they are merged into a single larger DetectionResult which is the union of the two rectangular DetectionResults.

Classification Step

The ClassificationStep class represents a composite classification analysis of a specific set of detection results. Similar to the DetectionStep, it can be made up of multiple independent algorithms and will result in a single array of IntermediateReportEntries (no more than one per DetectionResult).

Concurrent Multiple Pass Architecture

The software of the present invention allows for multiple analysis methods to be configured for the same region(s) within the tube, and may be configured such that the results of each method are attributed to a different analysis report group.

Figure 4B:
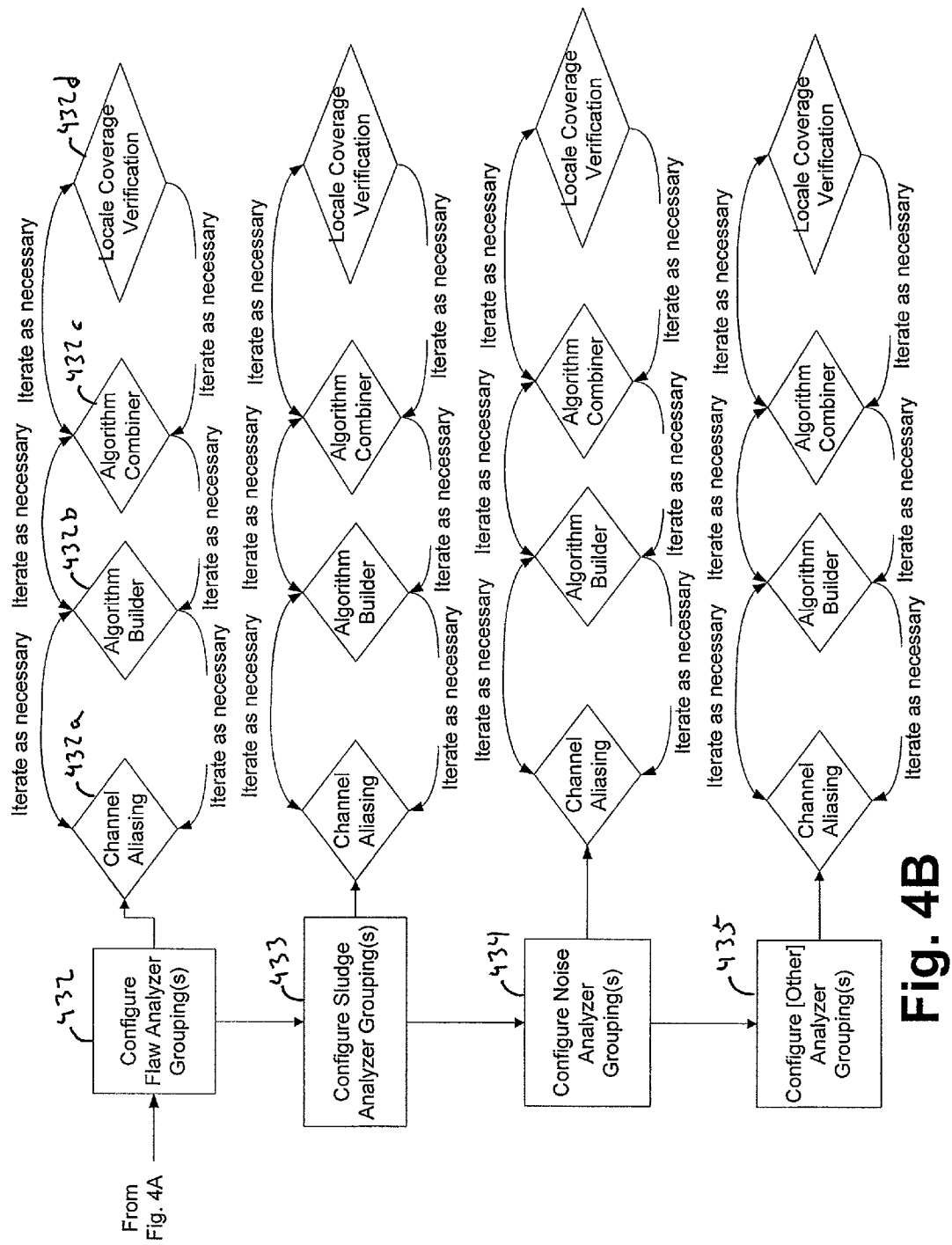
Figure 5A:
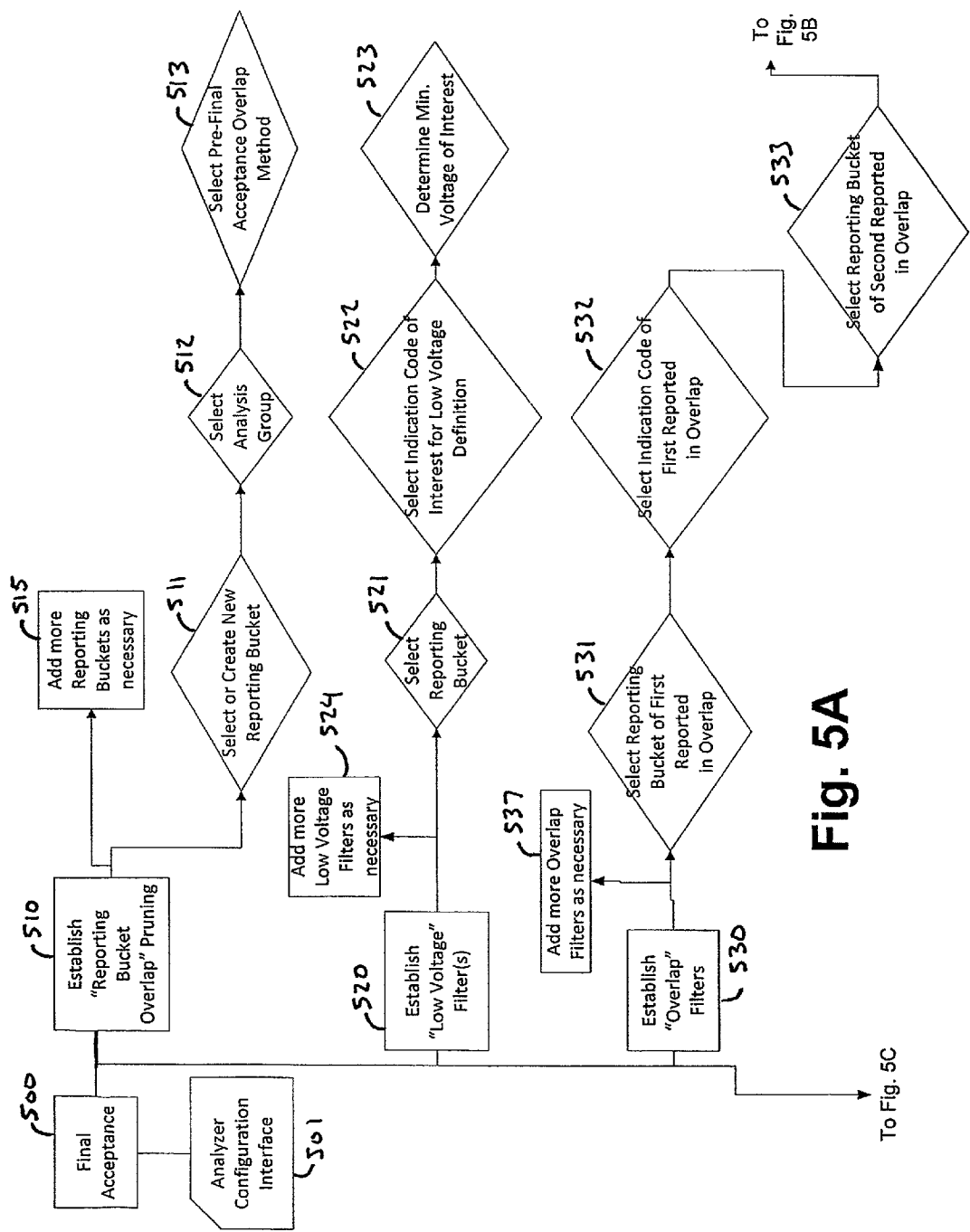
Figure 5B:
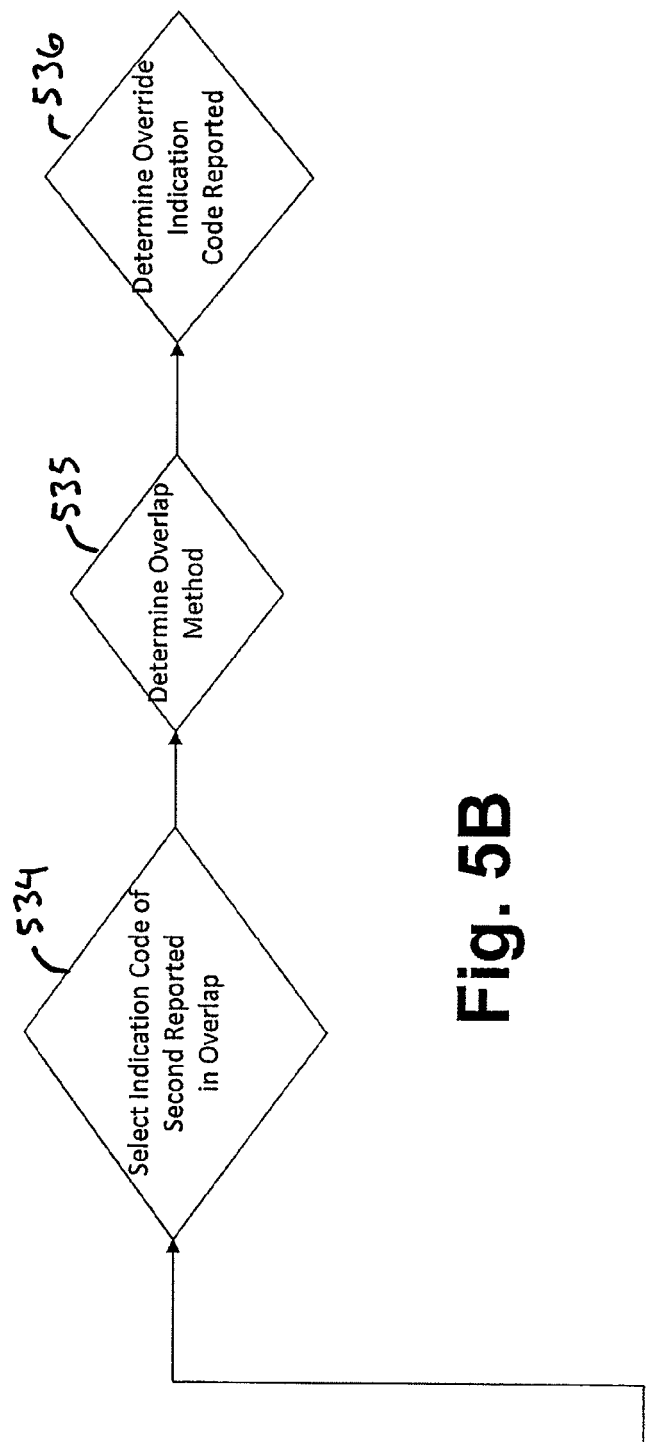
Figure 5E:
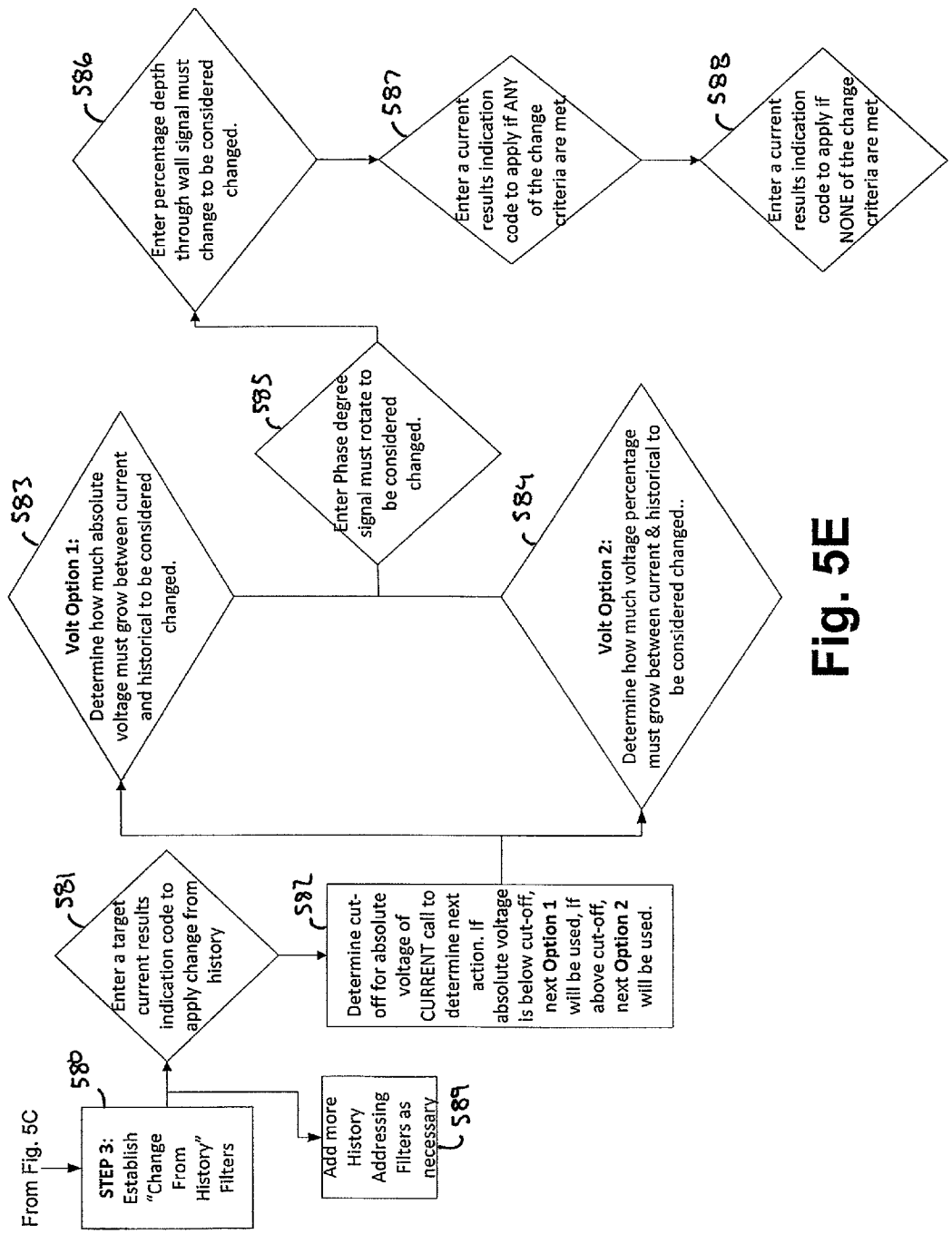

The Concurrent Multiple Pass Architecture is described in FIGS. 4a-b.

At step 410 Reporting Groups are created and confirmed. The action of Creating and Verifying report groups 412 each reporting pass is performed through a Site Configuration interface 411.

At step 420, Reporting Buckets are created, through an Analyzer Configuration Interface 421. This step comprises assigning Analysis Groups 422 and Assigning an overlap and pruning method 423.

At step 430, Multi-pass Analyzer Groupings are configured into a in single analyzer configuration. This is performed through the Site Configuration, Algorithm Training Interface, Analyzer Configuration Interfaces 431. At steps 432 Flaw Analyzer Groupings are configured by performing Channel Aliasing 432a, Algorithm Building 432b, Algorithm Combining 432c and Locale Coverage Verification 432d. These stages are explained in detail in the text that accompanies FIGS. 6a-6c, corresponding to the following referenced items: Channel Aliasing 610, Algorithm Building 620, Algorithm Combining 660 and Locale Coverage Verification 670. A similar process is performed for configuring Sludge Analyzer Groupings 433, Noise Analyzer Groupings 434 and analyzer groupings for other conditions 435.

In this fashion, Sludge may be run concurrently with Dents and/or normal Flaw analysis for example. Overlap of report entries in this case is deliberately allowed, however the report entries are segregated by analysis grouping in the report entry display.

Frequency Ratios/Deltas

Previous attempts at automated analysis have done a fair job at characterizing the traits a signal should have at a given frequency or set of frequencies for it to be considered a specific kind of damage mechanism. However, in many cases it is the behavior of the signal across frequencies which is of particular interest. Does it rotate at least 10 degrees from the primary frequency to the half prime frequency? Is the voltage at least 25% bigger on the primary frequency than it is on the half prime frequency? These are the kinds of criteria which ultimately determine whether the signal we are trying to characterize is a flaw and of what type. The present invention analysis product's rule based classification algorithm package allows for any number of ratio and/or direct difference measurements to be made between frequencies for any or all of the test subtypes; voltage, angle, depth and length.

Channel Aliases

There is a significant amount of variation in eddy current inspection parameters across generators and customers, from tubing variations and site preferences. However, analysis of the data has a large degree of commonality due to the basics of eddy current analysis. To permit working in generalities while targeting site specific situations when configuring analysis of data, the channel alias was created. It essentially permits analyzing data in terms of the concept of a particular class of data stream. For example, bobbin detection of flaws will generally take the prime frequency differential channel into consideration. This may be channel 1, 3, or even 169 for the bobbin coils of an XProbe. It will have varying frequencies depending on the generator. However, each of these instances can be referred to as BobbinDiff.High. Each acquisition technique has a mapping of actual channel to alias.

For process channels, there is a list of names indicative of the purpose of the process channel.

The alias also supports adding on named data filters. A collection of filter settings are named by the user, and may be specialized per technique. This specialization provides the ability to adjust filters based on specifics like pull speed. For example, a median filter needs its window adjusted based on sample density. In addition, 301 slices can be defaulted to, but increase or decrease as necessary for different settings.

The aliases then are used for detection and classification settings. This allows the settings to target the damage mechanisms basic presentation and be taken from one technique to another with minimal modification.

Final Acceptance

The RevospECT Final Acceptance Process provides innovation to the Eddy current analysis industry by relating analysis results being gathered real time in the field with data that has been gathered in previous analysis passes. This "Cross-Outage" view of the data allows for complex relations to be drawn across multiple data-sets, which allows for seeing rates of change in Steam Generators that occur over long periods of time. Additionally, the Final Acceptance Process allows for gathering and relating indications of interest (including Noise that breaks threshold) that are gathered real time, and evaluates these indications in their entirety, rather than just as single units, to determine patterns that can be drawn that present larger issues in the steam generator.

Auto Final Acceptance (FA) is a software component that automatically applies analyst-configured rules to reduce various forms of overcall that would result from using certain high probability of detection (POD) automated analysis methods. Running many detection/classification techniques in parallel increases POD but generates many redundant results that would be seen as overcall, but FA overlap rules automate the selection of a single final result to report from amongst the many redundant results.

FA merge rules automate the reporting of a single result that represent many similar results that might all be in some rule-specified proximity along the tube being tested. FA low voltage rules automatically discard overcalls that would result from applying very sensitive (i.e. high POD) detection thresholds. FA history match/address/compare rules provide an automated determination of whether the system overall is appropriately reporting or not reporting what it should, and prevents the low voltage rules from discarding history-matching results that also just happen to be small.

The Final Acceptance Process is described in FIGS. 5a-5e.

Final Acceptance is configured through the Analyzer Configuration Interface 501. At step 510 reporting bucket overlap pruning is established 510 through the steps of selecting an existing reporting bucket or creating a new one 511, selecting an Analysis Group 512 and selecting a Pre-final Acceptance Overlap Method 513. Additional reporting buckets are added and configured if necessary 515.

At step 520, Low Voltage Filters are Established by electing a Reporting Bucket 521, selecting an indication code of interest for a low voltage definition 522 and determining a minimum voltage of interest for the selected reporting bucket 523. More low voltage filters are established as necessary 524.

At step 530 Overlap Filters are established. This is done by selecting a reporting bucket of a first reported overlap 531, selecting an indication code of a first reported overlap 532, selecting a reporting bucket of a second reported overlap 533, selecting an indication of a second reported overlap 534, determining an overlap method 535 and determining an override indication code 536. More overlap filters are added as necessary 537.

At step 540, Multiple Indication Merge Filters are established. These filters establish where multiple indications in relative proximity are merged into a single indication. The steps to this process are: select a report bucket to determine merge viability 541, select and indication code of interest to determine merge viability 542, determine minimum proximity at which indications are considered for merging 543, and determine an indication code for merged indications reported 544. The process of establishing Multiple Indication Merge Filters is repeated for as many report buckets as necessary 545.

At step 550, History Addressing Filters are established. This process has three sub-steps, Limiting the scope of current historical results to be examined for comparison and identifying unaddressed results will be tagged 560, establishing relation criteria between historical and current results 570 and establishing "change from history" filters 580. The sub-steps of each of these processes (560, 570 and 580) are discussed as follows: Limiting the scope of current historical results to be examined for comparison and identifying unaddressed results 560 comprises: selecting a Current Results Analysis Group of interest 561, establishing Probe Codes of interest 562, and identifying new indication codes for indication codes that were unaddressed in the historical results 563. The step of establishing relation criteria between historical and current results 570, comprises: selecting an indication code in the current results 571, selecting an indication code in the historical results 572, determining the minimum proximity historical results and current historical results needed to be considered for addressing 573, determining a cut off for absolute voltage of historical data to determine the next step 574, if the absolute voltage is below the cut off minimum, determine the maximum voltage that a signal can shrink in the current result for the historical results to still be compared for associated change 575, if the absolute voltage is above the cut off minimum then determine the maximum voltage percentage that a signal can shrink in the current results for the historical results to still be considered for associated change 576. More history addressing filters can be added as necessary 577.

The step of establishing "change from history" filters 580 entails: entering a target current results indication code to apply "change from history" 581, determining a cut off for absolute voltage of the current data to determine the next action 582, if the current voltage is below the cut off, then determine how much the absolute voltage must grow between the current and historical values to be changed 583, or if the current voltage is above the cut off, determining how much the voltage percentage must grow between the current and historical data to be considered changed 584. Next, the user enter the amount the phase degree signal must be rotated to be considered changed 585. The percentage depth through wall signal that must changed to be considered changed is entered 586. The current results code to be applied if any of the change criteria are met is entered 587, and a current results indication code to apply if none of the change criteria are met is entered 588. More history addressing filters are added if necessary 589.

Historical Report Compare

Historical Report Compare is a software component that automatically applies analyst-configured rules to perform inspection history related decisions. The rules determine whether a result from a current inspection "matches elevation" with history, "addresses" history, and/or is "changed from" history, and whether to report the result with appropriately modified fields.

The configurable elevation-matching criteria allow analysts to specify elevation tolerances and probe codes to consider. The configurable address history criteria include tolerance on voltage and angle shrinkage rejection thresholds, and adjustment of the result's indication code that should appear in the final report. The configurable change-from-history criteria include voltage and angle thresholds, supporting absolute comparisons for small values and percentage comparisons for large values.

Locale Mapping

Presented below are the functional details for the Locale Mapping-related components of the present invention. It should be noted that Local Mapping has been divided into three sub-sections: 1) General; 2) Algorithms; and 3) Locating Schemes.

Graphical Locale Display

The present invention uses a locale concept to generalize settings to certain areas of the generator, such as the tubesheet, freespan, etc. specific to each leg. The Locale Chart provides a varying display of the locales present alongside the strip chart. The Locale Chart is a fixed width, displaying between 2 and 4 levels of locales, depending on the locales that exist in the data shown. The locales are highlighted if the data cursor falls in them, and there are various modes of navigating and zooming the data with the mouse.

Edge Correction

Edge corrections are a simple method by which the user can effectively add or subtract a fixed distance to the auto located edges of the support structures, tubesheets and/or tubeends. This allows a subtle control over our resultant locale mapping such that the user can choose to increase (or decrease) the amount of data allocated to a specific kind of support structure and it's internal edges region at the expense of data allocated to the freespan (typically). Each landmark structure type is allowed a specific configuration point for edge correction, so for instance broached supports may be given an additional ½ inch whereas solid supports may be given no correction.

Damage Mechanisms

The DamageMechanism class is the data structure responsible for mapping a named damage mechanism to any number of related analysis locales and the appropriate indication code(s). The DamageMechanism name is used along with the AnalysisLocale description string to map algorithms to location specific damage mechanisms. The DamageMechanism class is meant to be a setup related object, and is used to guide the user setting up auto analysis. Once damage mechanisms have been created and mapped to locales, setting up auto analysis consists of the user visiting each locale and picking a detection and/or classification method for each of the predetermined mechanisms mapped to that locale. Only those damage mechanisms which can be found in that particular locale are to be offered for the user to configure, and any left unconfigured can be easily warned of and/or tracked for later verification.

Locale Mapping-Related Algorithms

Expansion Transition Detection

Automatic detection of expansion transitions—an important part of the locale tree map structuring—is a precursor to the detection of circumferential cracks which, typically, lie in the neighborhood of the transition. Most circumferential cracks are located adjacent to support structure or an expansion transition. Automated identification of the expansion transition signal indication would play a key role in searching within "high confidence zones" for circumferential cracks among others.

Bobbin

The steepest infinitesimal gradient of the portion of the absolute prime frequency channel being analyzed is a point of interest. This point is determined by locating the slice corresponding to the maximum absolute value of the differential of the signal. An additional relative magnitude test is performed at this point across the calibrated absolute prime and locator frequency which discriminates between a false call and a hit.

X-Probe

In this case, the steepest infinitesimal gradient of the portion of the particular channel in the prime frequency display set is a point of interest. This particular channel corresponds to that which yields maximum voltage across the length of each portion of the channels contained in the display set. The steepest infinitesimal gradient on this channel is determined as in the bobbin case. In addition, the phase in the neighborhood of this point of interest across all display set channel must lie within a specified range in order to be confirmed as a true expansion transition location.

U-Bend Transition Detection

Prior knowledge of the number of u-bend transition points to identify is required in the algorithm. If a single point is required, the steepest infinitesimal gradient of the portion of the absolute prime frequency channel is determined. This location is identified by locating the slice corresponding to the maximum absolute value of the differential of the signal. As an additional discriminator, a relative voltage check with a user-supplied one performed in the neighborhood of the point of interest.

A similar analysis is performed when two u-bend transition points are required except that the duo points of interest are determined by selecting the two localized maxima in the signal. Relative voltage checks are performed in the neighborhood of both points as in the single u-bend case.

Sludge Detection (Bobbin)

The algorithm determines a null position in the neighborhood of a support plate or tube sheet signal. Using this null point as a reference it performs a polar coordinate discrimination of the signal elements which lies outside of a prescribed voltage and two phase boundaries. Elements within the preset polar domain are the sludge signal components.

Adaptive Threshold Detection

Threshold determination for discriminating signal from noise plays a crucial part in the overall detection process. In order to keep false call rate and miss rate at a minimum, the selected threshold must bear a direct relationship with the ambient signal to noise ratio. In other words, the threshold must adapt to the prevailing statistical properties of the signal being analyzed.

FIG. 2 shows a sub-section of a differential bobbin signal "substrate" sparsely riddled with signal indications due to flaws or tube support plates. The "substrate" corresponds to noise which contains no intellectual information for the purpose of eddy current analysis. The intent of the adaptive threshold process is to take advantage of the statistical properties in the noisy substrate to project a threshold based on different levels of detection sensitivity.

Definition: Standard Deviation (SD)

In probability and statistics, the standard deviation of a probability distribution, random variable, or population or multi-set of values is a measure of statistical dispersion of its values. The standard deviation is usually denoted with the letter σ (lower case sigma). It is defined as the square root of the variance.

The standard deviation of a random variable X is defined as:

$$\sigma = \sqrt{E((X - E(X))^2)}$$
$$= \sqrt{E(X^2) - (E(X))^2}$$
$$= \sqrt{\mathrm{Var}(X)}$$

Application of Standard Deviation in Adaptive Thresholding

Figure 3:
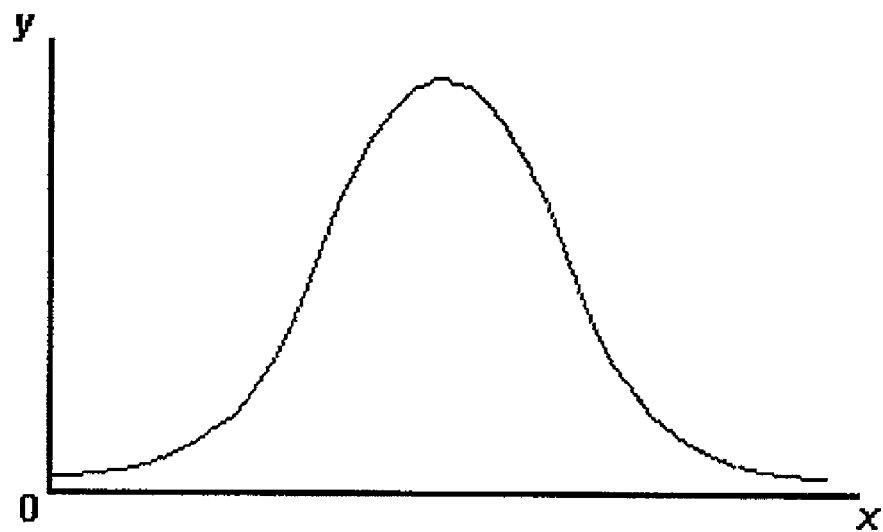
FIG. 3 depicts a normal distribution.

It is assumed that the voltages corresponding to noise in eddy current data in normally distributed. Statistically, for a large set of measurements about 68% will lie within one standard deviation of the average value, 95% will lie within 2 and 99.7% will lie within 3. This rule of thumb typically applies to population values with a normal distribution. FIG. 3 depicts normally distributed data on a graph.

Figure 3A:
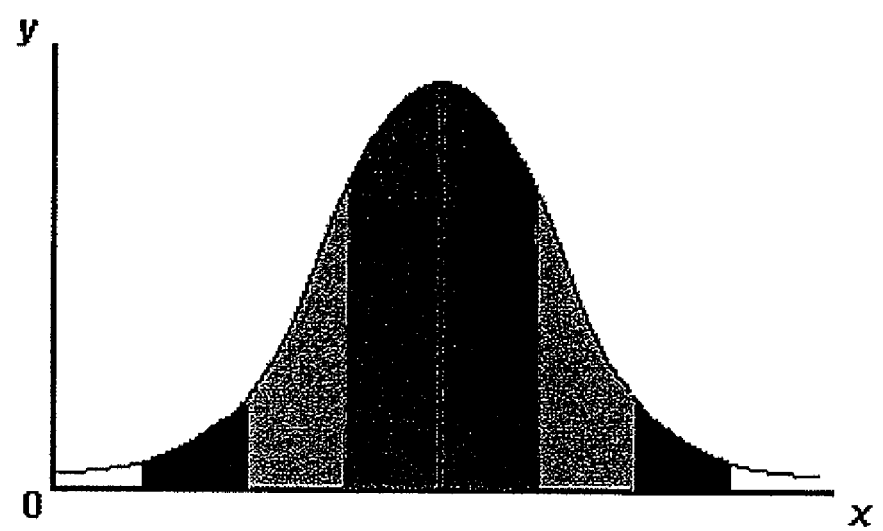
FIG. 3a depicts a normal distribution showing portions bounded by standard deviation from the mean.

FIG. 3a shows the normal distribution curve bounded by standard deviation from the mean. One standard deviation away from the mean in either direction on the horizontal axis (the red area on the above graph) accounts for somewhere around 68 percent of the data population corresponding to noise. Two standard deviations away from the mean (the red and green areas) account for roughly 95 percent of the population corresponding to noise. And three standard deviations (the red, green and blue areas) account for about 99 percent of the population corresponding to noise.

A variant of the standard deviation is used for eddy current adaptive thresholding. By replacing the mean with the median in equation (1), the median absolute deviation is obtained with proves to be more stable and less dependent on the extremes in population values.

By assuming that the pool of statistical properties in the eddy current signal such as volts peak-to-peak (vpp) or vertical max (vmx) follows a normal distribution, we estimate thresholds below which will contain approximately 100% of the noise distribution. The sensitivity is related to the number of times we wish to raise the threshold above the median absolute deviation.

Usage

As an initial test case, there are 10 levels available to vary the critical threshold based on the median absolute deviation. These are denoted as sensitivity levels. A sensitivity of 1 raises the multiplicative factor of the standard deviation much more than a sensitivity of 10. For x-probe and MRPC (maximum residual packet capacity) two-dimensional data representation, the following threshold is defined in the adaptive sense as follows:

$$\Omega = \mu + 2\xi\sigma\sqrt{\log(N)}$$

Where
Ω=threshold
μ=median value in the distribution
ξ=multiplier
σ=median absolute deviation
N=number of elements in the distribution. By empirical determination, N is set to 2.7184 until the number of elements in the distribution is above 5000.

Typically, the two-dimensional data is filtered to achieve a flat or level terrain. Examples of suitable filters are the median or CWT (continuous wavelet transformation) filters. Threshold determination for bobbin data is computed using direct multiples of the median value of a sufficiently large number of Vpp's in the population i.e.

$$\Omega = \xi\sigma$$

Where
Ω=threshold
ξ=multiplier
σ=median absolute deviation from the pool of Vpp values To enhance speed of computation for large population, sampling methods using random selection are used for computing the median.

With sufficient training data, the appropriate sensitivity level can be estimated for data collected in similar ambient conditions.

Locating Schemes

Auto Locating—Signal Formation

The present invention analysis allows for every landmark type to have its own specific set of criteria to be used by the autolocating algorithms. In particular, signal rotation for each type is now calibrated and stored during the setup process. During autolocating, the landmark type in question is determined for each landmark we attempt to detect and the appropriate rotation is then applied to the data prior to application of the algorithm. Each signal in question is only considered for further scrutiny if it is forming in the expected direction.

Auto Locating—Landmark Table Definability

Autolocating improvements were achieved in large part by improved definition of our landmark table. Exact information regarding which landmarks we expect to see at any given row and column is now available, along with logic for handling the 'gray areas' where landmark visibility comes and goes from outage to outage. Specific landmark widths and visibilities can be given overrides at specific row/column locations. This information may be used to describe places where the angle of the landmark's contact to the tube is different and therefore the landmark appears larger, or it may be employed to effectively combine two landmarks which are becoming very close in proximity to the point of appearing as one larger structure.

Avb elevations are now used by the autolocating software and are considered to be referenced from the apex of the ubend.

Auto Locating—Symmetry Considerations

The present invention analysis autolocating assumes, unless indicated otherwise by the landmark table, that the landmark structures in the ubend will be laid out in a symmetric fashion (but not necessarily equidistant). In this case, detection of landmarks in the ubend is done a pair at a time once the apex of the ubend has been determined. If symmetry is expected then the autolocating software requires that each pair of landmarks be detected at similar distances (within tolerances) from the apex of the ubend. Symmetry can be defined via the landmark table editor by placing an Apex marker in the landmark table (or two flanking markers in the event of one landmark being *at* the apex). If avb elevations relative to the apex are also supplied (in the case of a square bend), symmetry considerations become inferior to direct elevation usage and are ignored.

Algorithm Training Interface

All algorithms of the present invention are configured in a customized training interface, which provides a means to create detection and/or classification algorithms and test them on live data. During testing of the algorithm, key algorithmic steps such as dynamic threshold determinations, measurement locations, angle and voltage determinations, pass/fail status, etc. are stored in the program for subsequent review by the operator. Thus, the operator may step forward and back through the analysis process at will and view the exact details of how the currently configured algorithm performed its analysis. At each step information may be available to the system to automatically train in or out a signal of interest While the invention has been described in detail and with reference to specific examples thereof, it will be apparent to one skilled in the art that various changes and modifications can be made therein without departing from the spirit and scope thereof.

What is claimed is:

1. A system for the comprehensive monitoring, analysis and managing of tubing flaws, said system comprising:
   a computer platform whose architecture involves a distributed processing system for supporting parallel execution of automated analysis tasks, said platform comprising a locale analyzer and a detection classification unit for pinpointing tubing flaws;
   means for channel aliasing for analyzing data in terms of a particular class of datastream;
   an auto final acceptance means that automatically applies analyst-configured rules to reduce forms of overcall that would result from using high probability of detection automated analysis methods; and
   locale mapping means for generating settings to certain areas of the tubing and associated components, said locale mapping means implementing landmark edge correction, mapping a damage mechanism to a plurality of related analysis locales, and algorithms that involve expansion transition detection, adaptive threshold detection and locating schemes.

2. The system of claim 1 further comprising an algorithm training interface.

3. The system of claim 1 wherein said detection classification unit comprises a plurality of ratio or different measurements to be made between frequencies for voltage, angle, depth and length of said tubing.

4. A method for the comprehensive monitoring, analysis and managing of tubing flaws, said method comprising:
   loading and calibrating historical data and acquired data on a computer platform;
   sorting said historical and acquired data by locale;
   mapping said data for generating settings to certain areas of the tubing and associated components;
   detecting flaws based on said mapped data;
   classifying said flaws using at least one ratio or direct difference measurement between frequencies for at least one of the group consisting of voltage, angle, depth and length; and
   applying analyst-configured rules for reducing overcall and for selecting a single final result to report from among a plurality of redundant results.

5. The method of claim 4 further comprising the step of utilizing channel aliases to permit analyzing said data of a particular class of a data stream.

6. The method of claim 4 wherein said step of mapping comprises implementing landmark edge correction.

7. The method of claim 4 wherein said step of mapping comprises mapping a damage mechanism to a plurality of related analysis locales.

8. The method of claim 4 wherein said step of mapping comprises implementing algorithms that involve expansion transition detection.

9. The method of claim 4 wherein said step of mapping comprises implementing algorithms that involve adaptive threshold detection.

10. The method of claim 4 wherein said step of mapping comprises implementing algorithms that involve locating schemes.

* * * * *